(12) United States Patent
Hamidi

(10) Patent No.: US 9,782,343 B2
(45) Date of Patent: *Oct. 10, 2017

(54) METHOD AND SYSTEM FOR SYNTHESIZING NANOCARRIER BASED LONG ACTING DRUG DELIVERY SYSTEM FOR MORPHINE

(71) Applicant: Mehrdad Hamidi, Tehran (IR)

(72) Inventor: Mehrdad Hamidi, Tehran (IR)

( * ) Notice: Subject to any disclaimer, the term of this patent is extended or adjusted under 35 U.S.C. 154(b) by 2 days.

This patent is subject to a terminal disclaimer.

(21) Appl. No.: 14/337,044

(22) Filed: Jul. 21, 2014

(65) Prior Publication Data

US 2015/0017228 A1  Jan. 15, 2015

(51) Int. Cl.
| | |
|---|---|
| *A61K 9/16* | (2006.01) |
| *A61K 9/00* | (2006.01) |
| *A61K 31/485* | (2006.01) |
| *A61K 9/127* | (2006.01) |
| *A61K 9/51* | (2006.01) |

(52) U.S. Cl.
CPC .......... *A61K 9/0019* (2013.01); *A61K 9/1271* (2013.01); *A61K 9/1277* (2013.01); *A61K 9/5123* (2013.01); *A61K 9/5138* (2013.01); *A61K 9/5146* (2013.01); *A61K 9/5161* (2013.01); *A61K 9/5192* (2013.01); *A61K 31/485* (2013.01)

(58) Field of Classification Search
CPC .. A61K 9/0019; A61K 9/1271; A61K 9/1277; A61K 9/5123; A61K 9/5138; A61K 9/5146; A61K 9/5161; A61K 9/5192; A61K 31/485
See application file for complete search history.

(56) References Cited

U.S. PATENT DOCUMENTS 5,244,678 A * 9/1993 Legros ............... A61K 9/127
424/450

OTHER PUBLICATIONS

Anonymous. Malvern Instruments [online]; downloaded from <URL http://www.azonano.com/article.aspx?ArticleID=1220> on Oct. 28, 2015; 4 pages.*
Mady et al. J. Adv. Res. 2010; 1: 187-191.*
Hsieh et al. J. Food Sci. 2002; 67(8): 2808-2813.*
Grant et al. Anesth. Analg. 1994; 79: 706-709.*
Jain NK et al. Tropical J. Pharm. Res. 2014; 13(5): 661-668.*
Benson. Expert Opin Drug Deliv. 2006; 3(6): 727-737.*
Manosroi et al. Colloids and Surfaces B: Biointerfaces. 2003; 30: 129-138.*

* cited by examiner

*Primary Examiner* — David Browe
(74) *Attorney, Agent, or Firm* — Barry Choobin; Patent 360

(57) ABSTRACT

The embodiments herein provide a nano-carrier system for delivering a long-acting injectable drug of morphine and a method of synthesising the same. The morphine entrapped nanoparticles are prepared using a lipid/phospholipid core which is coated by a polymer. The lipid and phospholipid are dissolved in organic solvent. This solution is transferred into an aqueous phase consisting of distilled water or a buffer. A solution of polymer is added drop wise. The drug entrapped nanoparticle formation is achieved by diffusion of the organic solvent within the aqueous solvent to obtain the nanoparticles. The drug gets entrapped within the nanoparticles via the anti-solvency effect of the aqueous matrix. The resulting drug nanocarriers are capable of releasing the drug in a slow rate upon injection. The synthesized drug carrying nanoparticles are cryopreserved stored for future administration. For better storage, the nanodispersion is dried to form a powder.

6 Claims, 7 Drawing Sheets

Figure 1:
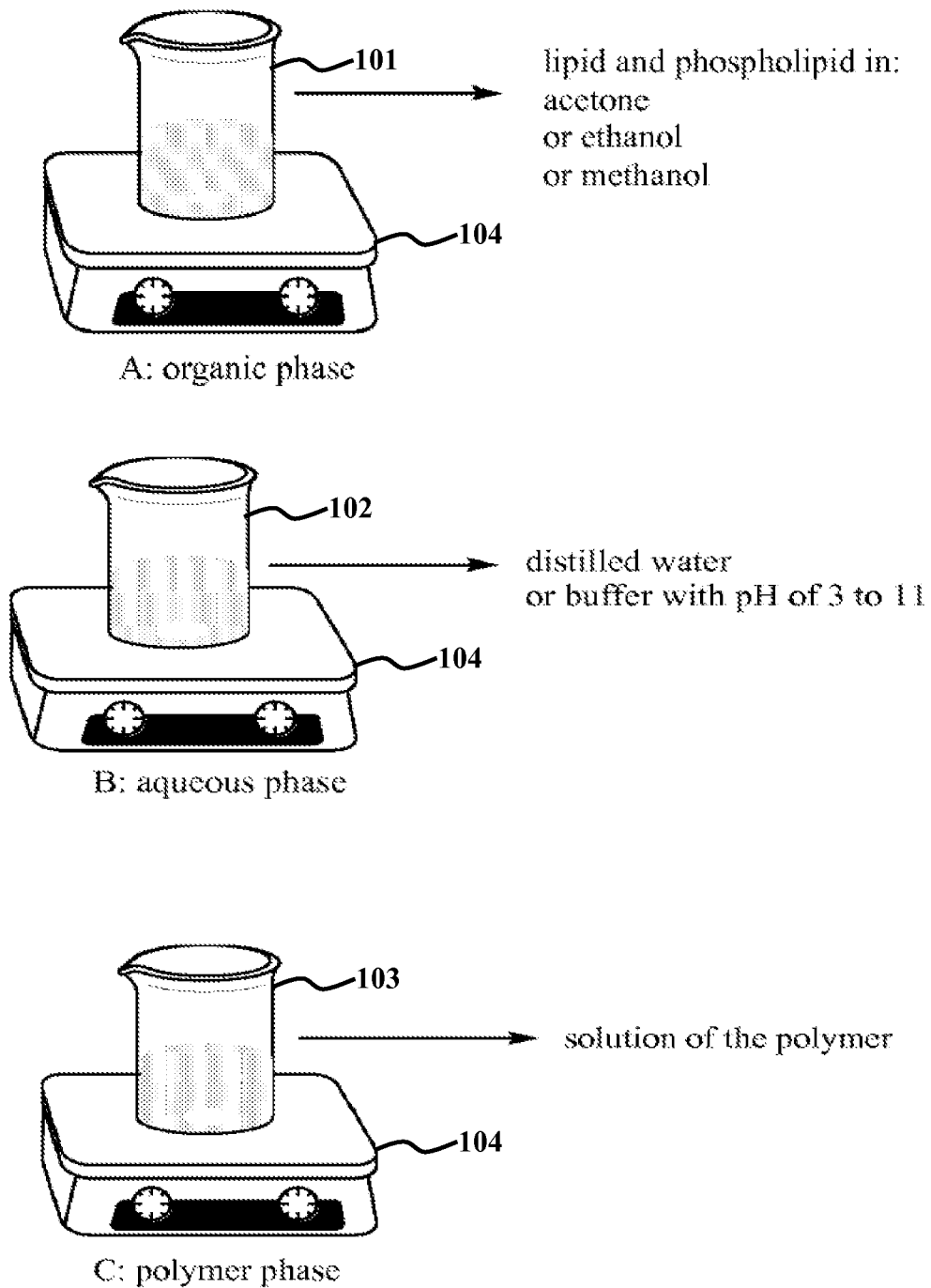

METHOD AND SYSTEM FOR SYNTHESIZING NANOCARRIER BASED LONG ACTING DRUG DELIVERY SYSTEM FOR MORPHINE

CROSS-REFERENCE TO RELATED APPLICATIONS

This application claims the priority of U.S. Provisional Patent Application No. 61/856,751 filed on Jul. 21, 2013 with the tile, "Long-Acting Injectable Dosage Form Based on Nanotechnology for Morphine", and the content of which is incorporated herein by reference in its entirely.

BACKGROUND

Technical Field

The embodiments herein generally relate to the field of molecular nanotechnology. The embodiments herein particularly relate to nanomedicines or nanocarrier based drug delivery systems. The embodiments herein more particularly relate to a system and method for synthesizing long acting, and slow release nanoparticle or nanocarrier based drug delivery system for morphine Description of the Related Art In nanotechnology, a particle is defined as a small object that becomes a whole unit with respect to its transport and properties. The particles are further classified according to the diameter. The "nanoparticles" have a diameter within a range of 1 and 100 nanometers.

Nanotechnology has offered many advantages for novel drug delivery systems in terms of both time-controlled drug delivery and site-directed drug delivery. These advantages are mainly derived from the very small (submicron) sizes of the nanostructures used as nanocarriers for drugs as well as the possibility of engineering the carrier structure and/or surface according to the particular biological requirements.

"Nanomedicine" is the medical application of nanotechnology. Nanomedicine ranges from the medical applications of nonmaterial's to nano-electronic biosensor and even possible future applications of molecular nanotechnology.

The current problems for nano-medicine involve understanding the issues related to toxicity and the environmental impact on a nanoscale material.

The nano-medicine has provided the possibility of delivering drugs to specific cells using nanoparticles. The overall drug consumption and side effects are lowered significantly by depositing an active agent only in a morbid region at a required and appropriate dosage thereby eliminating a need for a higher dosage.

Drug delivery researchers are developing nanoscale particles or molecules to improve a "bioavailability" of a drug. The term bioavailability refers to the presence of drug molecules where they are used in the body and where they act against an ailment. Drug delivery system mainly focuses on maximizing the bioavailability both at specific places in the body and over a period of time.

The drug delivery systems such as lipid or polymer based nanoparticles are designed to improve the pharmacological and therapeutic properties of the drugs. Further, the metal based nanoparticles are also designed and developed to deliver the drugs.

The commonly used metals for nano-drug delivery system include but not limited to gold, silver, platinum etc. The metal based nanoparticles for the drug delivery system show toxicity. The recent studies in this arena have shown that positively charged gold nanoparticles are found to enter kidney, while negatively charged gold nanoparticles remained in the liver and spleen. The positive surface charges of the nanoparticles decreases the rate of opsonization of nanoparticles in the liver, thereby affecting the excretory pathway. Even a relatively small size of the nanoparticles such as 5 nm can become compartmentalized in the perinephral tissues, and accumulate in the body over tissues. The advancement of research proves that targeting and distribution can be augmented by nanoparticles and the dangers of nano-toxicity have become an important question for the medical use in drug delivery.

A drug may cause tissue damage, but a drug delivery with regulated drug release can eliminate the problem. When a drug is removed too quickly from the body, this rapid drug delivery could force a patient to use a dose higher than a necessary dose. But a clearance can be reduced with drug delivery systems by altering the pharmacokinetics of the drug. A poor bio-distribution is a problem that can affect normal tissues through a widespread drug distribution, but the particulates from the drug delivery systems lower the volume of distribution and release the effect on a non-target tissue. The potential nano-drugs works by very specific and well understood mechanisms, one of the major impacts of nanotechnology and nano-science is the development of completely new drug delivery systems with more useful behaviors and less side effects.

Long-acting injectable drug delivery systems can benefit from the potentials of nanotechnology via the slow drug release from the nano-carriers already being loaded by the drug of interest. These drug carriers may be administered by injection into the host body through different routes mainly including intravenous, intramuscular, subcutaneous, intradermal, intra-arterial, intra-thechal, and intra-cardiac administration. Basically, a drug dose loaded in a nano-carrier is administered and the carrier, then supplies the drug needed for the particular pharmacological effect for a more extended time following a single dose compared to a conventional bolus dose. The pharmacokinetic outcome of the injectable long-acting dosage form is expected to be the lack of fluctuations in plasma concentrations of the drug which, eventually, results in avoiding the risks of over dosages, i.e., toxicity, or under dosages, i.e., treatment failure, in drug therapy. When a particular drug is administered in a chronic (long-term) basis in the form of repeated doses, a fluctuation in drug concentrations in plasma is observed. These pharmacokinetic fluctuations directly result in pharmacodynamic fluctuations where the drug affects the site of action and experiences peaks and troughs at the same time of concentration changes or after a lag phase. These fluctuations in the drug concentration are highly risky for patient, in particular for a drug like morphine with narrow therapeutic index (small differences between therapeutic and toxic doses). With the conventional, currently available products of the drug in the market, there is always a risk for the patient to experience an overdosage (toxic effects in brain or other tissues) in the peak times or an underdosage (insufficient drug effect), both the stages are harmful for the patient.

Morphine is an opioid analgesic drug and the main psychoactive chemical in opium. In clinical medicine, morphine is regarded as the gold standard of analgesic used to relieve intense pain. Like other opioids such as oxycodone, hydromorphine and diacetylmorphine (heroin), morphine acts directly on the central nervous system (CNS) to relieve pain. The primary source of morphine is the chemical extraction from opium. Morphine is the most abundant opiate found in opium. It is one of at least fifty alkaloids of several different types present in opium. Morphine is primarily used to treat both forms of acute and chronic pains, myocardial infarction, breathlessness etc.

The adverse effects of morphine overdose or improper dosage are constipation, addiction (both psychological and physical), hypogonadism, hormone imbalance, asphyxia, acute respiratory depression, renal failure (due to accumulation of metabolites in kidney), chemical toxicity, raised intracranial pressure, biliary colic, alteration in gene expression, adverse effect on immune cells etc.

The morphine is one of the most effective and most widely used narcotic analgesics. The analgesic drugs with well known indications in the relief of moderate to severe pains as well as the treatment of opioid dependence. The formulation of a long-acting product from morphine has a potential to improve the patient outcome as well as the patient comfort so that the overall success of chronic therapy with this drug is resulted obviously from the achievement of a long time activity of the drug in vicinity of the site of action with a reasonable concentration. The lipid based as well as polymeric-based nanoparticles are prepared and loaded by the drug morphine which serves as a drug reservoir capable of releasing the drug for long time periods in blood circulation, upon entry to the host body via injection. This long-term drug profile is used as a basis for prolonged chronic drug action toward the desired effects.

Hence there is a need to develop a nanoparticle based drug delivery system for morphine without any threat of cytotoxicity. Also there is a need for a nanoparticle drug delivery system for morphine to release the drug slowly and in a controlled manner to an action site. Further there is a need to develop a method for synthesizing the organic biomolecule based nanoparticle drug delivery system for morphine.

The above mentioned shortcomings, disadvantages and problems are addressed herein and which will be understood by reading and studying the following specification.

OBJECTIVES OF THE EMBODIMENTS

The primary objective of the embodiments herein is to synthesize a nano carrier based long acting drug delivery system for morphine using a lipid core coated with a polymer.

Another objective of the embodiments herein is to synthesize the drug carrying nanoparticles or nanocarrier entrapping morphine within the nanoparticles.

Yet another objective of the embodiments herein is to synthesize the drug nanocarrier based long acting drug delivery system for morphine to provide a controlled release of the drug at a slow rate upon administration to an individual.

Yet another objective of the embodiments herein is to synthesize the drug nanocarrier based long acting drug delivery system for morphine to enable an administration of a drug through intravenous, intramuscular, subcutaneous, intra-dermal, intra-arterial, intra-thecal and intra-cardiac routes.

Yet another objective of the embodiments herein is to synthesize the drug nanocarrier based long acting drug delivery system for morphine by entrapping the drug using the anti-solvency effect of the aqueous matrix.

Yet another objective of the embodiment herein is to synthesize the drug nanocarrier based long acting drug delivery system for morphine to cryoprotect the drug nanocarrier for future use and application.

These and other objects and advantages of the embodiments herein will become readily apparent from the following detailed description taken in conjunction with the accompanying drawings.

SUMMARY

The various embodiments herein provide a system and a method for the synthesis of the nanocarrier based drug delivery for morphine. The drug carrying nanoparticles or nanocarriers are prepared using a lipid/phospholipid core coated with a polymer. The nanocarriers entrap the morphine drug for site directed drug delivery and slow release.

According to one embodiment herein, morphine is an opioid analgesic drug, and the main psychoactive chemical in opium. In clinical medicine, morphine is regarded as a standard analgesic for the treatment of an intense pain. Like other opioids such as oxycodone, hydromorphone and diacetylmorphine (heroin), morphine acts directly on the central nervous system (CNS) to relieve the pain. Morphine is primarily used to treat both acute and chronic severe pains. It is also used for treating the pain due to myocardial infarction and for labor pains. Immediate administration of morphine is beneficial in reducing the symptoms of acute shortness of breath due to cancer and non-cancerous causes. In case of advanced cancer or end stage of cardio-respiratory diseases, a regular low dose with sustained release of morphine significantly reduces the breathlessness safely. Morphine is used as analgesic substitute in the patients intolerant to the drugs such as methadone or buprenorphine.

According to one embodiment herein, a method is provided for synthesizing slow and controlled release of a morphine entrapped in nanoparticle or nanocarrier. The method comprises the steps of dissolving a morphine in an organic solvent to get an organic solution. The morphine is dissolved at a concentration of 0.1 to 10 mg/ml in the organic solvent. The organic solvent is 0.1 to 5 mg/ml. A phospholipid is added to the organic solution to form a bilayer around the morphine. A lipid is added to the organic solution to obtain an organic solution mixture, and the organic solution mixture comprises organic solvent dissolved with the morphine, phospholipid and lipid. The organic solution mixture is added drop wise or in drops to an aqueous solution to form a lipid core, and the pH of the aqueous solution is in a range of 3-11. A volume ratio of the organic solution mixture to the aqueous solution is within range of a 0.05 to 3. A buffered solution of a polymer is added to the aqueous solution with lipid core to form a coating layer around the lipid core to obtain a nano carrier. The pH of the polymer solution is in a range of 3.5 to 11. The polymer solution is added drop wise to the aqueous solution in a volume ratio of 0.05 to 1.

The organic solvent is selected from a group consisting of a methanol, an ethanol, an acetone and an isopropanol. The phospholipid is selected from a group consisting of a phosphatidylcholine, a phosphatidylethanolamine, a phosphatidylinositol. The lipid is selected from a group consisting of a monostearyl glycerol, a distearyl glycerol, a palmitic acid, a stearic acid and a glyceryl stearate. The polymer is selected from a group consisting of a chitosan, a polyethylene glycol, a polyvinyl alcohol.

According to one embodiment herein, a system is provided for a slow and controlled release of a morphine entrapped in nanoparticle or nanocarrier. The system comprises a core of aqueous phase or solution, a lipid layer, a phospholipid bilayer embedded with the morphine and a polymer coating. The aqueous solution is made of water or a buffer. The phospholipid is selected from a group consisting of a phosphatidylcholine, a phosphatidylethanolamine, a phosphatidylinositol. The lipid is selected from a group consisting of a monostearyl glycerol, a distearyl glycerol, a palmitic acid, a stearic acid and a glyceryl stearate. The polymer is selected from a group consisting of a chitosan, a polyethylene glycol, a polyvinyl alcohol.

The morphine is water-insoluble and is present in a phospholipid bilayer during a formation of a nanovesicle. The morphine gets loaded to the nanocarriers in a dissolved state within a thickness of the bilayers. The morphine nanocarrier or nanoparticle particle size distribution curve exhibit a peak of 128.5 nm, and wherein morphine nanocarrier has a relative low polydisparity index of 0.180. The morphine nanocarrier or nanoparticle has a zeta potential within a range of 10 mv to 30 mv. The morphine nanocarrier or nanoparticle has a zeta deviation of 4.71 mv. The morphine nanocarriers or nanoparticles are administered intravenously, intramuscularly, sub-cutaneously, intra-dermally, intra-arterially, intra-thecaly and intra-cardiac routes.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The other objects, features and advantages will occur to those skilled in the art from the following description of the preferred embodiment and the accompanying drawings in which:

FIG. 1 illustrates a schematic representation of the processes for the preparation of organic phase, aqueous phase and polymer phase solutions in the method for synthesizing a nano-carrier based long acting drug delivery system for morphine, according to an embodiment herein.

FIG. 2 illustrates a schematic representation of a method for synthesizing a nano-carrier based long acting drug delivery system for morphine, according to an embodiment herein.

FIG. 3 illustrates a flowchart indicating a method for synthesizing a nano-carrier based long acting drug delivery system for morphine, according to an embodiment herein.

FIG. 4 illustrates a graph indicating a size distribution profile of the drug nano-carriers for morphine, according to an embodiment herein.

FIG. 5 illustrates a graph indicating the zeta potential distribution profile of the drug nano-carriers/nanoparticles for morphine, according to one embodiment herein.

FIG. 6 illustrates a graph indicating the drug release profile of morphine from a nano-carrier based long acting drug delivery system for morphine, according to one embodiment herein.

FIG. 7 illustrates a schematic structure of a nano-carrier based long acting drug delivery system for morphine, according to one embodiment herein.

Although the specific features of the embodiments herein are shown in some drawings and not in others. This is done for convenience only as each feature may be combined with any or all of the other features in accordance with the embodiments herein.

DETAILED DESCRIPTION OF THE EMBODIMENTS

In the following detailed description, a reference is made to the accompanying drawings that form a part hereof, and in which the specific embodiments that may be practiced is shown by way of illustration. The embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

The various embodiments herein provide a system and a method for the synthesis of the nanocarrier based drug delivery for morphine. The drug carrying nanoparticles or nanocarriers are prepared using a lipid/phospholipid core coated with a polymer. The nanocarriers entrap the morphine drug for site directed drug delivery and slow release.

According to one embodiment herein, morphine is an opioid analgesic drug, and the main psychoactive chemical in opium. In clinical medicine, morphine is regarded as a standard analgesic for the treatment of an intense pain. Like other opioids such as oxycodone, hydromorphone and diacetylmorphine (heroin), morphine acts directly on the central nervous system (CNS) to relieve the pain. Morphine is primarily used to treat both acute and chronic severe pains. It is also used for treating the pain due to myocardial infarction and for labor pains. Immediate administration of morphine is beneficial in reducing the symptoms of acute shortness of breath due to cancer and non-cancerous causes. In case of advanced cancer or end stage of cardio-respiratory diseases, a regular low dose with sustained release of morphine significantly reduces the breathlessness safely. Morphine is used as analgesic substitute in the patients intolerant to the drugs such as methadone or buprenorphine.

According to one embodiment herein, a method is provided for synthesizing slow and controlled release of a morphine entrapped in nanoparticle or nanocarrier. The method comprises the steps of dissolving a morphine in an organic solvent to get an organic solution. The morphine is dissolved at a concentration of 0.1 to 10 mg/ml in the organic solvent. The organic solvent is 0.1 to 5 mg/ml. A phospholipid is added to the organic solution to form a bilayer around the morphine. A lipid is added to the organic solution to obtain an organic solution mixture, and the organic solution mixture comprises organic solvent dissolved with the morphine, phospholipid and lipid. The organic solution mixture is added drop wise or in drops to an aqueous solution to form a lipid core, and the pH of the aqueous solution is in a range of 3-11. A volume ratio of the organic solution mixture to the aqueous solution is within range of a 0.05 to 3. A buffered solution of a polymer is added to the aqueous solution with lipid core to form a coating layer around the lipid core to obtain a nano carrier. The pH of the polymer solution is in a range of 3.5 to 11. The polymer solution is added drop wise to the aqueous solution in a volume ratio of 0.05 to 1.

The organic solvent is selected from a group consisting of a methanol, an ethanol, an acetone and an isopropanol. The phospholipid is selected from a group consisting of a phosphatidylcholine, a phosphatidylethanolamine, a phosphatidylinositol. The lipid is selected from a group consisting of a monostearyl glycerol, a distearyl glycerol, a palmitic acid, a stearic acid and a glyceryl stearate. The polymer is selected from a group consisting of a chitosan, a polyethylene glycol, a polyvinyl alcohol.

According to one embodiment herein, a system is provided for a slow and controlled release of a morphine entrapped in nanoparticle or nanocarrier. The system comprises a core of aqueous phase or solution, a lipid layer, a phospholipid bilayer embedded with the morphine and a polymer coating. The aqueous solution is made of water or a buffer. The phospholipid is selected from a group consisting of a phosphatidylcholine, a phosphatidylethanolamine, a phosphatidylinositol. The lipid is selected from a group consisting of a monostearyl glycerol, a distearyl glycerol, a palmitic acid, a stearic acid and a glyceryl stearate. The polymer is selected from a group consisting of a chitosan, a polyethylene glycol, a polyvinyl alcohol.

The morphine is water-insoluble and is present in a phospholipid bilayer during a formation of a nanovesicle. The morphine gets loaded to the nanocarriers in a dissolved state within a thickness of the bilayers. The morphine nanocarrier or nanoparticle particle size distribution curve exhibit a peak of 128.5 nm, and wherein morphine nanocarrier has a relative low polydisparity index of 0.180. The morphine nanocarrier or nanoparticle has a zeta potential within a range of 10 mv to 30 mv. The morphine nanocarrier or nanoparticle has a zeta deviation of 4.71 mv. The morphine nanocarriers or nanoparticles are administered intravenously, intramuscularly, sub-cutaneously, intra-dermally, intra-arterially, intra-thecaly and intra-cardiac routes.

According to an embodiment herein, the drug carrying nanoparticles are prepared using a lipid/phospholipid core which is then, coated by a polymer. The lipid part, stearic acid, lipoic acid, monostearin, distearin, and cholesterol are used in conjugation with phospholipid part which acts as the stabilizer for the solid lipid. As the phospholipid part, phosphatidyl choline (lecithin) and/or phosphatidyl ethanolamaine are used. The chitosan, alginate, poly (vinyl alcohol), poly (ethylene glycol), poly (vinyl pyrrolidone) are the polymers used in this process for coating.

According to one embodiment herein, morphine is an opioid analgesic drug, and the main psychoactive chemical in opium. In clinical medicine, morphine is regarded as a standard analgesic used to relieve intense pain. Like other opioids such as oxycodone, hydromorphone and diacetylmorphine (heroin), morphine acts directly on the central nervous system (CNS) to relieve pain. Morphine is primarily used to treat both acute and chronic severe pains. It is also used for treating or relieving the pain due to myocardial infarction and labor pains. Immediate administration of morphine is beneficial in reducing the symptoms of acute shortness of breath due to cancer and non-cancerous causes. In case of advanced cancer or end stage of cardio-respiratory diseases, a regular and sustained release of a low dose of morphine significantly reduces breathlessness safely with the benefits/effects maintained over time. Morphine is used as analgesic substitute in the patients intolerant to the drugs such as methadone or buprenorphine. The structure of morphine is illustrated as below.

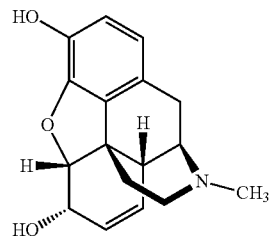

According to one embodiment herein, the first step in the process of synthesizing the morphine drug nanocarriers involves dissolving the lipid and phospholipid in an organic solvent. The organic solvent is chosen from a group comprising acetone, ethanol, and methanol. The concentration of the organic solvent is in the range of 0.1 to 5 mg/ml. The solution of lipid and phospholipid in an organic solvent is transferred into an aqueous phase consisting of distilled water or a buffer with pH of 3-11. The drug such as morphine to be entrapped in the nanoparticles/nanocarriers is present in the aqueous phase at a concentration of 0.1 to 10 mg/ml. The volume ratio of organic-to-aqueous phase mixture is within a range of 0.05-3. The mixture obtained is by adding a solution of the polymer to the organic-to-aqueous phase solution of morphine. The polymer solution is prepared in a buffered medium with a pH range of 3.5 to 11.0. The polymer solution is added drop-wise or in drops to the organic-to-aqueous phase mixture in a volume ratio of 0.05 to 1.

According to an embodiment herein, the nanocarriers are capable of releasing the morphine drug in a slow rate upon injection via intravenous, intramuscular, subcutaneous, intradermal, intrathecal and intracardiac routes.

According to one embodiment herein, the particle formation is achieved mechanistically by the diffusion (dilution) of the organic solvent within the aqueous host solvent to obtain the nano particles. The interested drug such as morphine is entrapped in the nanoparticles/nanocarrier via the antisolvency effect of the aqueous matrix. The basic method for the preparation of the phospholipid-based nanocarriers is known as "ethanol injection" with some modifications. In this method, the phospholipid, which is practically insoluble in water, is dissolved in a water-miscible solvent, typically ethanol. The ethanol is gradually added drop-wise or in drops to a higher amount of water (for example, 10-times the ethanolic solution volume). When the phospholipid comes into contact with ethanol in the water phase, ethanol "diffuses" into the water phase and becomes diluted leading to formation of new solvent which is mainly water with a small portion of the ethanol. Since the phospholipid cannot be dissolved in this new solvent and there is a vigorous shaking in system on the other hand, the amphiphilic phospholipids undergoes self-assemble process by using the vesicles made of phospholipid bilayers as their shells and an entrapped water phase as the core and the core is surrounded by the phospholipid bilayers. When a drug such as "morphine", which is insoluble in water, presents itself in the medium at the time of nanovesicle formation, morphine becomes loaded to the nanocarriers in a dissolved condition within the thickness of bilayers, as the only possibility for the morphine to stay in this medium in a thermodynamic point of view, during the formation of the self assemblies because the drug is hydrophobic and cannot be found in any proportion within the core of the surrounding waters.

According to one embodiment herein, the nanocarrier is has a lipid-phospholipid-polymer structure each of the components offer a definite property to the drug delivery system. The lipid fraction makes the system a suitable carrier for lipiphilic drugs such as morphine. The lipid fraction restricts the rapid release of the drug from the nanocarrier. The phospholipid component makes the system more amphiphilic to incorporate the lipophilic, the hydrophilic and the amphiphilic drugs. The presence of this phospholipid fraction offers the self assembly behaviour to the nanocarrier. The polymer forming a coating on the outer shell of the nanocarrier provides a surface charge, fluidity and mechanical strength.

According to one embodiment herein, the materials used for the synthesis of the drug nanocarriers/nanoparticles are divided into four groups. The four groups are organic solvents, phospholipids, lipids and polymers. The organic solvents which are used for the synthesis of the drug nanocarrier/nanoparticle are methanol, ethanol, acetone and isopropanol. The phospholipids which are used for the synthesis of the drug nanocarrier/nanoparticle are phosphatidylcholine, phosphatidylethanolamine and phosphatidylinositol. The lipids which are used for the synthesis of the drug nanocarrier/nanoparticle are monostearyl glycerol, distearyl glycerol, palmitic acid and stearic acid. The polymers which are used for the synthesis of the drug nanocarrier/nanoparticle are chitosan, polyethylene glycol, ad polyvinyl alcohol. The aqueous solution is a water or a buffer, which is used for the formation of the core.

According to one embodiment herein the drug such as morphine in different concentrations is taken for the preparation of the drug carrying nanoparticles/nanocarriers based on specific objectives, therapeutic dosages and indications. The drug such as morphine is then dissolved in organic solvent such as ethanol, methanol, or acetone to get a solution. The lipid (mainly a glyceryl stearate) is added in different amounts (quantities) to the solution of morphine and organic solvent. The lipid is added in a specific concentration depending on the drug and organic solvent concentrations. This solution mixture consisting of drug such as morphine, organic solvent and lipid is added drop wise or in drops into an aqueous phase (water or buffer) to form the lipid cores. The buffered aqueous solution of the polymer with different concentrations is added dropwise or in drops onto the cores based on the amounts or quantities of other compounds present in the solution to form the coatings or shells around the phospholipid core.

According to one embodiment herein, the nanoparticle/nanocarriers are subjected to in-vitro characterization tests, after the synthesis of morphine drug entrapped nanoparticle/nanocarriers.

According to one embodiment herein, the particle size distribution of the nano-dispersion is evaluated using the Dynamic Light Scattering (DLS) method. The surface zeta potential of the nano-dispersion is also evaluated by the electrophoretic mobility method. The drug release profile of the nanoparticles is most important factor and is analyzed in vitro.

According to one embodiment herein, the synthesized drug loaded nanoparticle/nanocarrier is dried to form a powder using a freezer-dryer. The freeze-drying process enables the better storage. Glucose, lactose, trehalose, sorbitol, glycerol, mannitol or Tween are used in a concentration of 0.25-5%, for cryopreservation, The characterization reveals an aqueous core with drug surrounded by a phospholipid bilayer. The lipid core is surrounded by the polymer shell. Two kinds of substances such as cryoprotectant and lyoprotectant are used for the cryopreservation by freeze-drying method of the drug loaded nanocarriers or nanoparticles. The role of cryoprotectant is to prevent irreversible aggregation of the nanoparticles during the freezing process. The cryoprotectant and lyoprotectant materials are mixed with the nanoparticles/nanocarriers (nano-dispersion) before drying. When the freezing process is carried out on the samples, the cryoprotectant and lyoprotectant materials provide either a physical barrier or an electrical barrier around each nanocarrier or align the particles in solid-liquid interfaces during the freezing process resulting in the protection of each individual carrier from being aggregated with the neighbouring particles. The lyoprotectants also play a similar role. The commonly used cryoprotectants and lyoprotectants are monosaccharides, disaccharides, polyols and non-ionic surfactants.

According to one embodiment herein, there are four mechanisms responsible for the drug release from a nanocarrier when administered to an individual. The mechanisms are passive diffusion, based on the Fickian kinetics, nanocarrier erosion occurring with time resulting in drug release, water penetration inside nanoparticles followed by channelling (the drug is dissolved and diffused based on the drug concentration gradient) and nanocarrier capture by the natural defence cells of the host body, then drug release out of the vehicle. These mechanisms contribute to the drug release from the nanocarrier.

FIG. 1 illustrates a schematic representation of the processes for the preparation of organic phase, aqueous phase and polymer phase solutions in the method for synthesizing a nano carrier based long acting drug delivery system for morphine, according to an embodiment herein. A lipid and a phospholipid are dissolved in an organic solvent in a beaker. The organic solvent are selected from an acetone or an ethanol or a methanol (101). The lipid and phospholipid are dissolved in the organic solvent by a magnetic stirrer 104. The drug such as morphine is then dissolved in organic solvent such as ethanol, methanol, or acetone to get a solution (101). The lipid (mainly a glyceryl stearate) is added in different amounts (quantities) to the solution of morphine and organic solvent. The lipid is added in a specific concentration depending on the drug and organic solvent concentrations. This solution mixture consisting of drug (morphine), organic solvent and lipid is added drop wise into an aqueous phase (water or buffer) to form the lipid cores (102). The buffered aqueous solution of the polymer with different concentrations is added dropwise onto the cores based on the amounts or quantities of other compounds present in the solution to form the coatings or shells around the phospholipid core. Finally, a buffered aqueous solution of the polymer such as a poly cation with a pH of 3.5 to 11 and a concentrations based on the amount of other compounds, is added dropwise onto the lipid cores to form the coating layers around the lipid cores (103) and the drug entrapped nanocarrier is obtained. The polymer solution is added dropwise to the organic to aqueous phase in a volume ratio of 0.05 to 1. The morphine is water insoluble and is present itself in the phospholipids bilayer. In a beaker, a lipid and phospholipids are dissolved in an organic solvent. The organic solvent is selected from an acetone or an ethanol or a methanol. The lipid and phospholipids are dissolved in the organic solvent by a magnetic stirrer.

Figure 2:
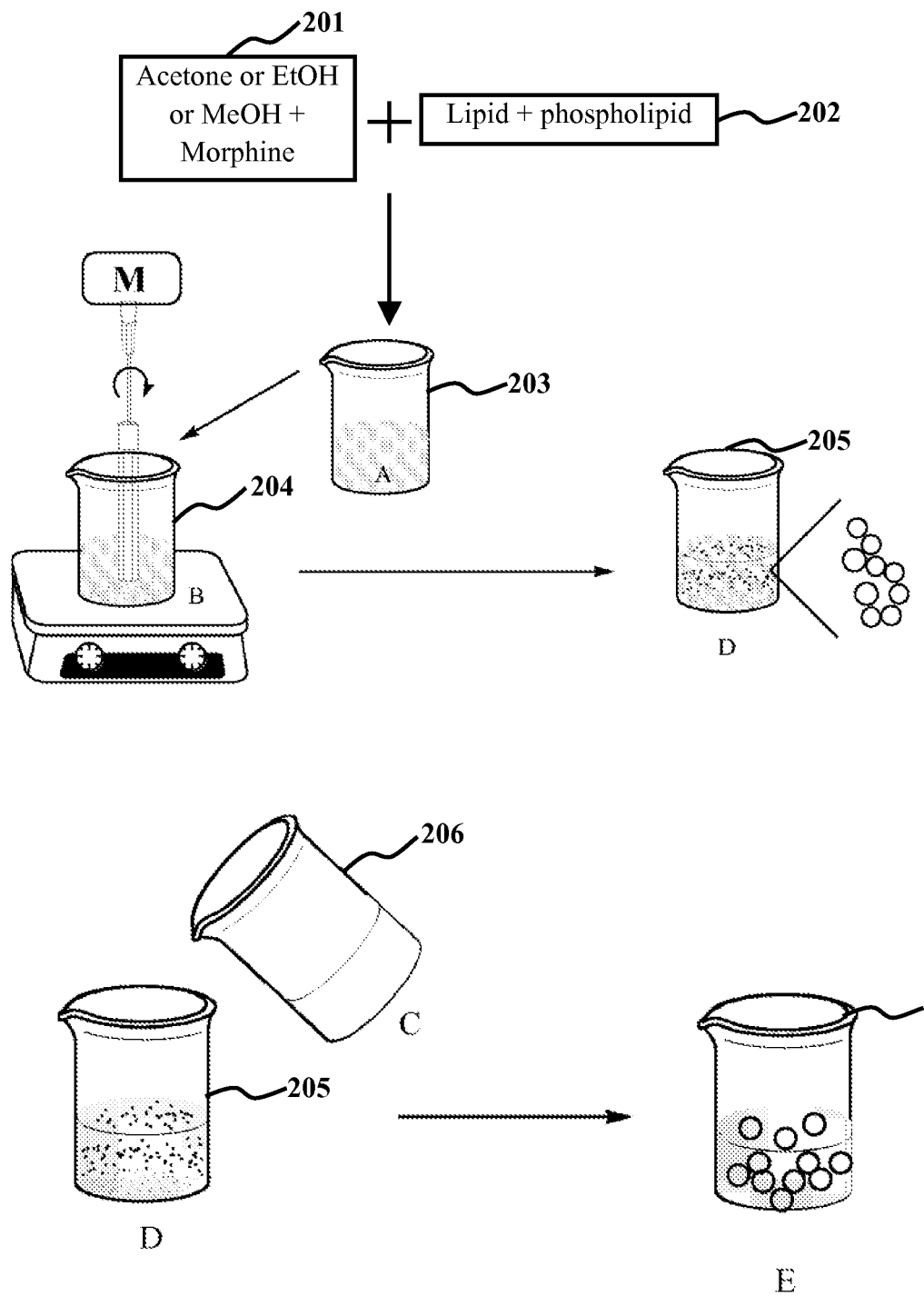

FIG. 2 illustrates a schematic representation of a method for synthesizing a nano carrier based long acting drug delivery system for morphine, according to an embodiment herein. The morphine in different salts concentration is taken based on the specific objectives, therapeutic dosages and indications. The morphine is dissolved in an organic solvent, ethanol, methanol or acetone (201). The organic solvent has a concentration of 0.1 to 5 mg/ml. The morphine to be entrapped is taken in the concentration of 0.1 to 10 mg/ml. Then different amounts of the phospholipid, mainly phosphatidylcholine, are dissolved in this solution and, finally, the lipid, mainly a glyceryl stearate, is dissolved in the same solution with a preset concentration depending on the drug and the organic solvent components (202). The mixing of organic solvent with morphine, lipid and phospholipid yields a solution mixture-A (203). The solution-A is added dropwise onto an aqueous phase B such as water or buffer with a pH in the range of 3-11 (204). The lipid cores-D are formed aqueous phase (205). The volume ratio of the organic to the aqueous phase mixtures is 0.05 to 3. Finally, a buffered aqueous solution of the polymer C such as a poly cation with a pH of 3.5 to 11 with different concentrations, based on the amount of other compounds, is added dropwise onto the lipid cores to form the coats around the lipid cores D (206) and the drug nanocarriers E are obtained (207). The polymer solution is added dropwise to the organic to aqueous phase in a volume ratio of 0.05 to 1. The morphine is water insoluble and presents itself in the phospholipid bilayer.

Figure 3:
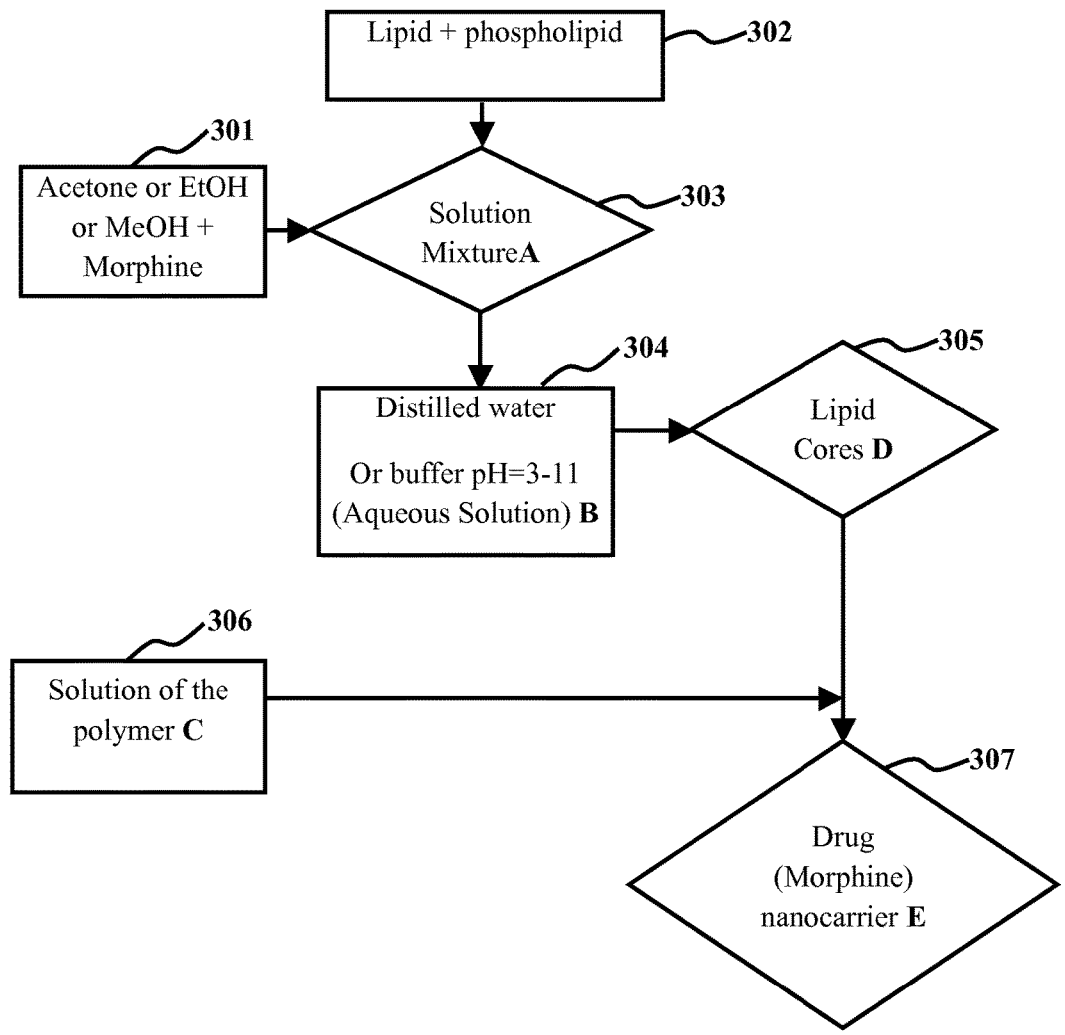

FIG. 3 illustrates a flowchart indicating a method for synthesizing a nano carrier based long acting drug delivery system for morphine, according to an embodiment herein. The morphine in different salts in different concentrations is taken based on the specific objectives, therapeutic dosages and indications. The morphine is dissolved in an organic solvent, ethanol, methanol or acetone (301). The organic solvent has a concentration of 0.1 to 5 mg/ml. The morphine to be entrapped is taken in the concentration of 0.1 to 10 mg/ml. Then different amounts of the phospholipid, mainly phosphatidylcholine, are dissolved in this solution and, finally, the lipid, mainly a glyceryl stearate, is dissolved in the same solution with a preset concentration depending on the drug and the organic solvent components (302). The mixing of organic solvent with morphine, lipid and phospholipid yields a solution mixture-A (303). The solution-A is added dropwise onto an aqueous phase B such as water or buffer with a pH in the range of 3-11 (304). The lipid cores-D are formed aqueous phase (305). The volume ratio of the organic to the aqueous phase mixtures is 0.05 to 3. Finally, a buffered aqueous solution of the polymer C such as a poly cation with a pH of 3.5 to 11 with different concentrations, based on the amount of other compounds, is added dropwise or in drops onto the lipid cores to form the coats around the lipid cores (306). The polymer solution is added dropwise to the organic to aqueous phase in a volume ratio of 0.05 to 1. The drug nanocarriers E comprising morphine are obtained (307). The morphine is water insoluble and presents itself in the phospholipid bilayer.

EXAMPLE 1

Synthesis of Morphine Carrying Nanoparticle/Nanocarrier

The following materials are required for the synthesis of nano carrier based drug delivery system for morphine
1. Organic solvent: methanol, ethanol, acetone, isopropanol;
2. Phospholipids: Phosphatidylcholine, phosphatidylethanolamine, phosphatidylinositol;
3. Lipids: Monostearyl glycerol, Distearyl glycerol, Palmitic acid, Stearic acid
4. Polymers: chitosan, polyethylene glycol, polyvinyl alcohol.

Procedure: In the first step based on the specific objectives, therapeutic dosages and indications the morphine at different salts in different concentrations is taken. The morphine is dissolved in an organic solvent, ethanol, methanol or acetone. The organic solvent has a concentration of 0.1 to 5 mg/ml. The morphine to be entrapped is taken in the concentration of 0.1 to 10 mg/ml. Then different amounts of the phospholipid, mainly phosphatidylcholine, are dissolved in this solution and, finally, the lipid, mainly a glyceryl stearate, is dissolved in the same solution with a preset concentration depending on the drug and the organic solvent components. The mixing of organic solvent with morphine, lipid and phospholipid yields a solution mixture-A. The solution-A is added dropwise onto an aqueous phase such as water or buffer with a pH in the range of 3-11. The lipid cores-C are formed aqueous phase. The volume ratio of the organic to the aqueous phase mixtures is 0.05 to 3. Finally, a buffered aqueous solution of the polymer such as a poly cation with a pH of 3.5 to 11 with different concentrations, based on the amount of other compounds, is added dropwise onto the lipid cores to form the coats around the lipid cores and the drug nanocarriers D are obtained. The polymer solution is added dropwise to the organic to aqueous phase in a volume ratio of 0.05 to 1. The morphine is water insoluble and presents itself in the phospholipid bilayer.

Figure 4:
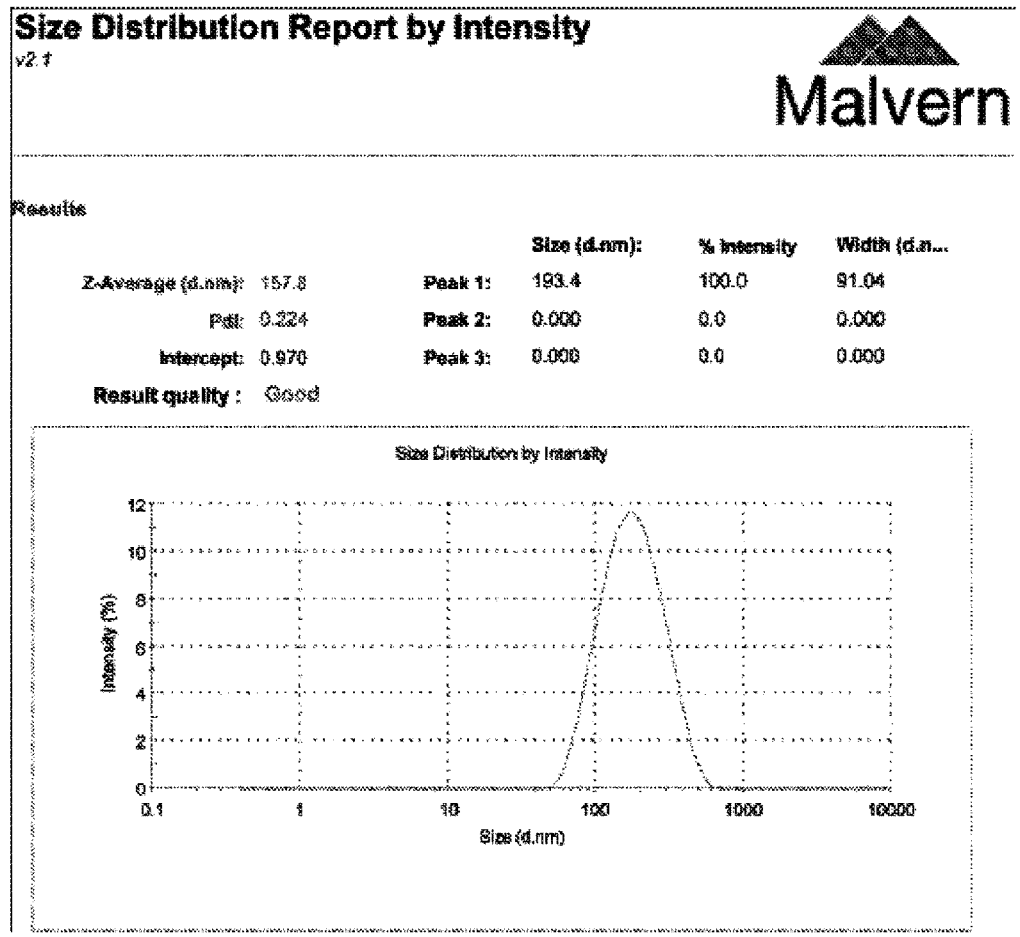

FIG. 4 illustrates a graph indicating a size distribution profile of the drug nano-carriers for morphine, according to an embodiment herein. With respect to FIG. 4, the particle size distribution of the nanoparticles is analyzed by DLS analysis. The curves in the graph of FIG. 4 are the long-normal probability curves. In the graph, log of the diameters of the nanoparticle populations is plotted against the relative contribution of the probability in the total number of particles based on the scattered light intensity from each sub-population. The particle size distribution curves in FIG. 4 exhibit only one peak (128.5 nm) with a relatively low polydispersity index (0.180). This indicates an ideal size of the nanoparticles with only one peak representing a unimodal size distribution.

Figure 5:
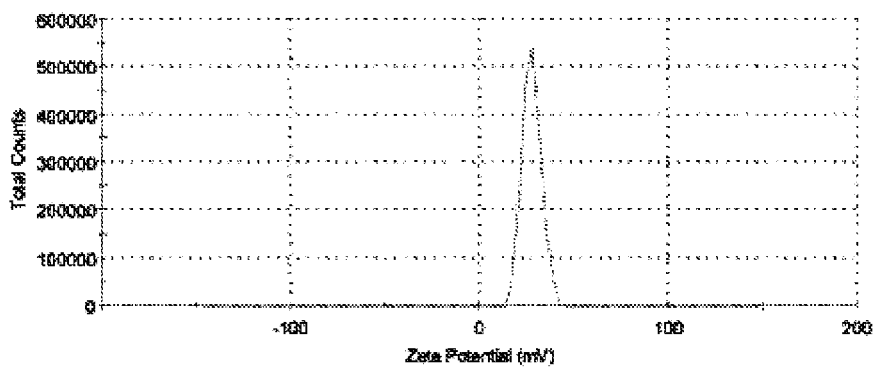

FIG. 5 illustrates a graph indicating the zeta potential distribution profile of the drug nano-carriers/nanoparticles for morphine, according to one embodiment herein. The zeta potential characterizes the electrical potential on the surface of a colloid. This parameter is of a particular importance both regarding the in vitro stability of the nanoparticles owing to the presence of a minimum electrical repulsion between the particles and also the in vivo fate of the nanocarrier upon entry to the host organism. The fate of the nanoparticles is regarding the effect of the surface potential on the capture of the nanoparticles by the natural defence mechanisms of the organism. The zeta potential required for the stability of the nanoparticles is 10 mv-30 mv. FIG. 5 shows the in vitro stability a potential of nanoparticles to be around 30 mv is ideal but not less than 10 mv. Also for the fate of the nanoparticles, a zeta potential between +30 mv and −30 mv is ideal, but the positive potential is the mostly preferred than neutral than negative, which is shown by the nanoparticles in FIG. 5. The FIG. 5 further illustrates the narrow distribution of the zeta potentials of the nanoparticles with a zeta deviation of 4.71 mv, is a very promising result along with the unimodal distribution (only one peak) of the zeta potentials which is again promising with respect to the homogeneity of the particles.

Figure 6:
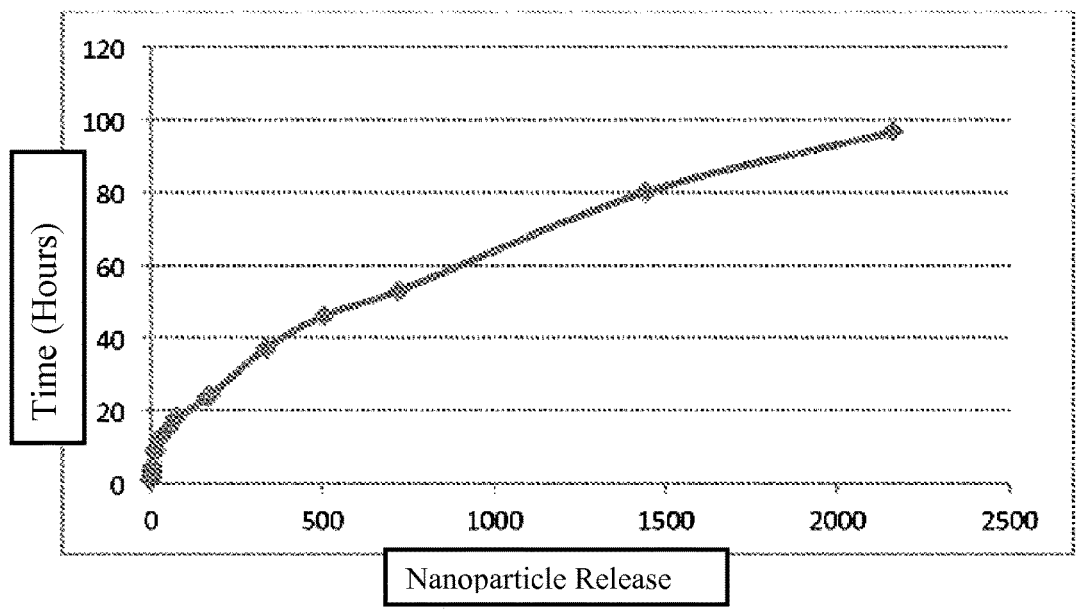

FIG. 6 illustrates a graph indicating the drug release profile of morphine from a nano carrier based long acting drug delivery system for morphine, according to one embodiment herein. In FIG. 6, the gradual release of the drug with a near-constant (a straight line) release rate is observed as an ideal behaviour of a controlled release system. FIG. 6 further illustrates the absence of a significant burst of drug release in initial stages. Also the considerable high plateau time of 36 hours is highly promising for obtaining a slow drug release system upon injection to the host body.

According to one embodiment herein, the slow release and the controlled release of the morphine is tested in vitro. A 3 ml of the nanocarrier dispersion is poured to a dialysis sac with an atomic mass of 12 KDa. The dialysis sac is placed in 50 ml phosphate buffer saline (PBS) which is stirred gently at 20 rpm at 37° C. At initial time such as time 0 and at the predetermined time intervals, 1 ml aliquot sample is removed from the external medium and is replaced with fresh PBS. The drug concentration in the aliquot sample is determined with reference to a blank free drug solution placed at the same condition. The test reveals the slow and controlled release of morphine from the nanocarrier or nanoparticle.

According to one embodiment herein, the morphine nanocarrier or nanoparticles have many advantages i.e. in the preparation of the nanocarriers popularly available raw materials are used. Also a cost-effective and simple method is used for the preparation of nanocarriers. The biosafety of all the ingredients used in this process is well-accepted globally, as highlighted by their approval for human use by United States Food and Drug Administration (USFDA). The average size of the nanocarriers prepared makes them, on one hand, very suitable for avoidance of the biological capture by the body defence mechanisms and, on the other hand, provides a practically reliable space for being loaded by an adequate amount of the drug. The uniformly mono dispersed particles provide a reproducible matrix to be loaded by the same amounts of the drug in different batches, a feature very important for the industrial production of the nanocarriers. The narrowly distributed positive electrical potential on the nanoparticles surfaces which offers a remarkable stability both in vitro and in vivo for the nanocarriers. The constant and slow rate of the drug release from the nanoparticles, assures a long acting drug delivery system as intended by the investigators. The morphine nanocarrier does not burst release the drug from the nanocarriers.

Figure 7:
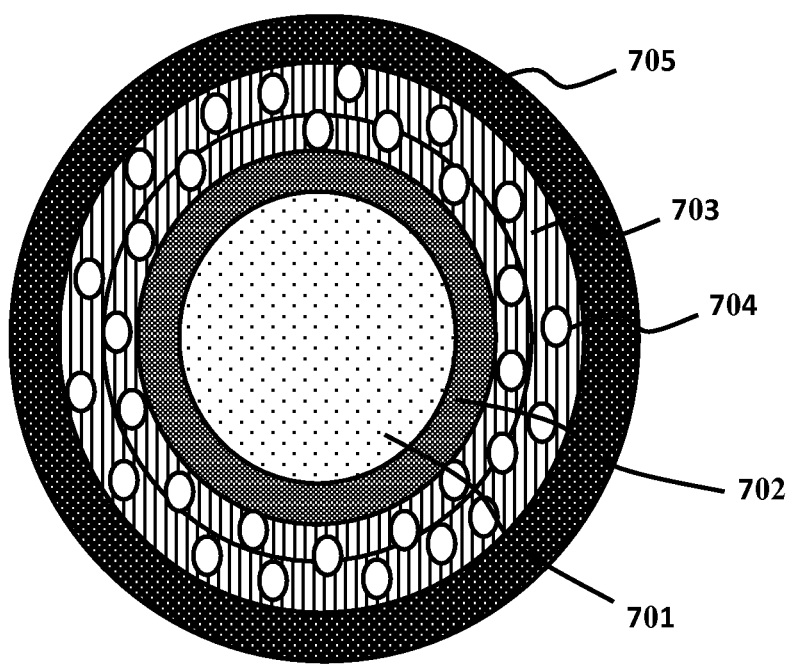

FIG. 7 illustrates a schematic structure of a nanocarrier based long acting drug delivery system for morphine, according to one embodiment herein. The nanocarrier drug delivery system for morphine comprises of an aqueous solution core 701. A lipid layer 702 is present around the aqueous solution. A phospholipid bilayer 703 is present around the lipid layer. The phospholipid bilayer has the entrapped or embedded morphine drug particles 704. The outermost layer or coating of the morphine drug nanocarrier is formed by a polymer 705. The organic solvent for dissolving the lipid and phospholipid is selected from a group consisting of a methanol, an ethanol, an acetone and an isopropanol. The aqueous solution is a water or a buffer, which forms the core. The phospholipid is selected from a group consisting of a phosphatidylcholine, a phosphatidylethanolamine, a phosphatidylinositol. The lipid is selected from a group consisting of a monostearyl glycerol, a distearyl glycerol, a palmitic acid, a stearic acid and a glyceryl stearate. The polymer is selected from a group consisting of a chitosan, a polyethylene glycol, a polyvinyl alcohol.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments.

It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

Although the embodiments herein are described with various specific embodiments, it will be obvious for a person skilled in the art to practice the invention with modifications. However, all such modifications are deemed to be within the scope of the claims.

It is also to be understood that the following claims are intended to cover all of the generic and specific features of the embodiments described herein and all the statements of the scope of the embodiments which as a matter of language might be said to fall there between.

What is claimed is:

1. A system for slow and controlled release of a morphine entrapped in nanoparticle or nanocarrier comprises:
    a core of aqueous phase or solution and wherein the aqueous solution is made of water or a buffer;
    a lipid layer present around the core aqueous phase, wherein the lipid is selected from the group consisting of monostearyl glycerol, distearyl glycerol, and palmitic acid;
    a phospholipid bilayer embedded with the morphine, the phospholipid bilayer is present around the lipid layer, wherein the phospholipid is selected from the group consisting of phosphatidylcholine, phosphatidylethanolamine and phosphatidylinositol; and
    a polymer coating forming an outermost layer, wherein the polymer is selected from the group consisting of polyethylene glycol and polyvinyl alcohol.

2. The system according to claim 1, wherein the morphine is water-insoluble and is dissolved within the phospholipid bilayer.

3. The system according to claim 1, wherein a size distribution curve of the nanoparticles or nanocarriers exhibits a peak of 128.5 nm and a relatively low polydispersity index of 0.180.

4. The system according to claim 1, wherein the nanoparticles or nanocarriers have a zeta potential within a range of 10 mv to 30 mv.

5. The system according to claim 1, wherein the nanoparticles or nanocarriers have a zeta deviation of 4.71 mv.

6. The system according to claim 1, wherein the nanocarriers or nanoparticles are administered intravenously, intramuscularly, sub-cutaneously, intra-dermally, intra-arterially, intra-thecaly and intra-cardiac routes.

* * * * *